US007195870B2

(12) United States Patent
Olek et al.

(10) Patent No.: US 7,195,870 B2
(45) Date of Patent: Mar. 27, 2007

(54) DIAGNOSIS OF DISEASES ASSOCIATED WITH GENE REGULATION

(75) Inventors: Alexander Olek, Berlin (DE); Christian Piepenbrock, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 493 days.

(21) Appl. No.: 10/239,676

(22) PCT Filed: Apr. 6, 2001

(86) PCT No.: PCT/EP01/03968

§ 371 (c)(1),
(2), (4) Date: Sep. 24, 2002

(87) PCT Pub. No.: WO01/77375

PCT Pub. Date: Oct. 18, 2001

(65) Prior Publication Data

US 2003/0082609 A1   May 1, 2003

(30) Foreign Application Priority Data

| Apr. 6, 2000 | (DE) | ............... 100 19 058 |
| Apr. 7, 2000 | (DE) | ............... 100 19 173 |
| Jun. 30, 2000 | (DE) | ............... 100 32 529 |
| Sep. 1, 2000 | (DE) | ............... 100 43 826 |

(51) Int. Cl.
*C12Q 1/68* (2006.01)
(52) U.S. Cl. ............. 435/6; 435/91.2; 536/24.31; 536/24.33
(58) Field of Classification Search .......... 435/6, 435/91.2; 536/24.31, 24.33
See application file for complete search history.

(56) References Cited

U.S. PATENT DOCUMENTS

| 6,812,339 B1 * | 11/2004 | Venter et al. ............ 536/24.31 |
| 6,977,146 B1 * | 12/2005 | Olek ............................ 435/6 |
| 2003/0036081 A1 | 2/2003 | Adorjan et al. |
| 2003/0113750 A1 | 6/2003 | Distler et al. |

FOREIGN PATENT DOCUMENTS

| WO | WO- 95 11995 A | 5/1995 |
| WO | WO- 99 28498 A | 7/1999 |
| WO | WO 01/68911 A2 | 9/2001 |
| WO | WO 01/68912 A2 | 9/2001 |
| WO | WO 01/76451 A2 | 10/2001 |
| WO | WO 01/77164 A2 | 10/2001 |
| WO | WO 01/77376 A2 | 10/2001 |
| WO | WO 01/77377 A1 | 10/2001 |
| WO | WO 01/81622 A2 | 11/2001 |
| WO | WO 01/92565 A2 | 12/2001 |
| WO | WO 02/00705 A1 | 1/2002 |
| WO | WO 02/00928 A1 | 1/2002 |
| WO | WO 02/02806 A3 | 1/2002 |
| WO | WO 02/02808 A1 | 1/2002 |
| WO | WO 02/012554 A1 | 2/2002 |
| WO | WO 02/36604 A1 | 5/2002 |
| WO | WO 02/36814 A1 | 5/2002 |

OTHER PUBLICATIONS

Herman et al. Methylation-specific PCR: A novel PCR Assay for methylation status of CpG islands. Proc. Natl.Acad. Sci., vol. 93, pp. 9821-9826, 1996.*
Liu et al. Fusion between transcription factor CBF beta/PEBP2 beta and a myosin heavy chain in acute myeloid leukemia. Science, vol. 261 (5124), pp. 1041-1044, 1993.*
Weiler et al. Hybridization based DNA screening on peptide nucleic acid (PNA) oligomer arrays. Nucleic Acids Res., vol. 25, No. 14, pp. 2792-2799, 1997.*
Laken et al. Genotyping by mass spectrometric analysis of short DNA fragments. Nature Biotechnology, vol. 16, pp. 1352-1356, 1998.*
Lowe et al. A computer program for selection of oligonucleotide primers for polymerase chain reactions. Nucleic Acids Research, vol. 18, No. 7, pp. 1757-1761, 1990.*
Rein, T., et al., (1988) "Identifying 5-methylcytosine and related modifications in DNA genomes", Nucleic Acids Research, vol. 26, No. 10 pp. 2255-2264, Oxford University Press.
Olek, A., et al., (1996) "A modified and improved method for bisulphite based cytosine methylation analysis", Nucleic Acids Research, vol. 24, No. 24, pp. 5064-5066.
Zeschnigk, M., et al., (1997) "A single-tube PCR test for the diagnosis of Angelman and Prader-Willi syndrome based on allelic methylation differences at the SNRPN locus" Eur J Hum Genetics, vol. 5, No. 2 pp. 94-98.
Olek, A., et al. (1997) "The pre-implantation ontogeny of the H19 methylation imprint", Nature Genetics, vol. 17, No. 3 pp. 275-276.
Gonzalgo, ML., et al., (1997) "Rapid quantitation of methylation differences at specific sitesusing methylation-sensitive single nucleotide primer extension (Ms-SNuPE)", Nucleic Acids Research, vol. 25, No. 12 pp. 2529-2531.
Xiong, Z., et al., (1997) "COBRA: a sensitive and quantitative DNA methylation assay", Nucleic Acids Research, vol. 25, No. 12 pp. 2532-2534.
Grigg, G., et al., (1994) "Sequencing 5-methylcytosine residues in genomic DNA" Bioessays, vol. 16, No. 6 pp. 431-436.
Zeschnigk, M., et al., (1997) "Imprinted segments in the human genome: different DNA methylation patterns in the Prader-Willi/Angelman syndrome region as determined by the genomic sequencing method", Human Molecular Genetics, vol. 6, No. 3 pp. 387-395.
Feil, R., et al., (1994) "Methylation analysis on individual chromosomes: Improved protocol for bisulphite genomic sequencing" Nucleic Acids Research, vol. 22, No. 4 pp. 695-696.

(Continued)

*Primary Examiner*—Suryaprabha Chunduru
(74) *Attorney, Agent, or Firm*—Barry L. Davison, J.D.; Davis Wright Tremaine LLP

(57) ABSTRACT

Chemically modified genomic sequences of genes associated with gene regulation, to oligonucleotides and/or PNA-oligomers for detecting the cytosine methylation state of genes associated with gene regulation which are directed against the sequence are disclosed. In addition, a method for ascertaining genetic and/or epigenetic parameters of genes associated with gene regulation is disclosed.

22 Claims, 1 Drawing Sheet

OTHER PUBLICATIONS

Figure 1:
Figure 1:
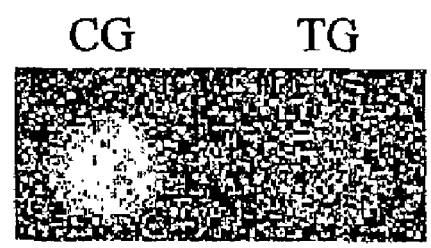

Martin, V., et al., (1995) "Genomic sequencing indicates a correlation between DNA hypomethylation in the 5'region of the pS2 gene and its expression in human breast cancer cell lines" Gene, vol. 157, pp. 261-264.

Database Embl; Accession No. X54156; XP002181265, Abstract.

Herman, James G., et al., "Methylation-Specific PCR: A Novel PCR Assay for Methylation Status of CPG Islands," Preceedings of the National Acadamy of Sciences of USA, National Academy of Science, Washington, US, vol. 93, pp. 9821-9826, 1996.

Mass, Marc J., et al. "Arsenic alters cytosine methylation patterns of the promotor of the tumor suppressor gene P53 in human lung cells: A model for a mechanism of carcinogenesis." vol. 386, No. 3, pp. 263-277, 1997.

Niemeyer C.M., et al., "DNA Microarrays," Angewandte Chemie, VCH Verlagsgesellschaft, Weinheim, DE, vol. 38, No. 19, pp. 3039-3043, 1999.

Rein, Thea, et al., "Identifying 5-methylcytosine and related modifications in DNA genomes" Nucleic Acids Research, Oxford University, Surrey, Great Britain, vol. 26, No. 10, pp. 2255-2264, 1998.

* cited by examiner

I
II

DIAGNOSIS OF DISEASES ASSOCIATED WITH GENE REGULATION

REFERENCE TO SEQUENCE LISTING

1. Field of the Invention

The levels of observation that have been well studied by the methodological developments of recent years in molecular biology, are the genes themselves, the translation of these genes into RNA, and the resulting proteins. The question of which gene is switched on at which point in the course of the development of an individual, and how the activation and inhibition of specific genes in specific cells and tissues are controlled is correlatable to the degree and character of the methylation of the genes or of the genome. In this respect, pathogenic conditions may manifest themselves in a changed methylation pattern of individual genes or of the genome.

The present invention relates to nucleic acids, oligonucleotides, PNA-oligomers and to a method for the diagnosis and/or therapy of diseases which have a connection with the genetic and/or epigenetic parameters of genes associated with gene regulation and, in particular, with the methylation status thereof.

2. Background of the Invention

The completion of the sequencing of the human genome has highlighted the need to further understand the regulation and control of genes. The cell exerts multiple levels of control over genes, however for the majority of genes the most important regulatory mechanism is transcriptional control.

There are multiple mechanisms of gene regulation involving different families of proteins, genes and regulatory sequences. The transcription of eukaryotic genes by polymerases requires the prior assembly of transcription factors at the promoter region of the gene. These factors bind in a specific order, beginning with the binding of TFIID to the TATA box. This provides several stages at which gene regulation may take place, and many eukaryotic gene regulation mechanisms are thought to work by exerting positive or negative control over these processes.

Gene regulatory proteins recognise short stretches of double stranded DNA. Hundreds of such sequences have been identified throughout the genome, e.g. Sp1, which recognises the sequence GGGCGG (in double stranded form), GATA-1 which recognises the sequence TGATAG (in double stranded form) and Oct-1 which recognises ATG-CAAAT (in double stranded form). Gene regulatory proteins contain structural motifs that are able to recognise the regulatory sequences using the unique pattern of hydrogen bond donors, hydrogen bond acceptors and hydrophobic patches in the major and minor groove of the DNA. Several famillies of structural motifs are known, including the helix-turn-helix motif, comprised of amino acids, the zinc finger motif, which utilises one or more molecules of zinc as a structural component, the leucine zipper and helix-loop-helix motif.

Other mechanisms of gene regulation include chromatin packaging. Chromatin that is highly compacted is incapable of transcription, and in a less condensed form, DNA is still packaged on nucleosomes. Nucleosomes positioned at the beginning of a transcription site block the assembly of transcription factors, and these must be removed. In addition gene transcription requires extensive winding and unwinding of the supercoiled DNA. Although the exact mechanisms of DNA packaging are not completely understood, they include the use of a variety of DNA helicases, gyrases and topoisomerases. Further discussion of gene regulation may be found in standard molecular biology textbooks e.g. Alberts et. al. 'Molecular Biology of the cell' Garland Publishing.

Disruptions to gene regulation pathways have been implicated in a wide variety of diseases including, for example, but not limited to:

Severe combined immunodeficiency disease:Misaki et. al. 'Gene-Transferred Oligoclonal T Cells Predominantly Persist in Peripheral Blood from an Adenosine Deaminase-Deficient Patient during Gene Therapy.' Mol Ther 2001 January;3(1):24–27.

Cardiac damage: Pieper et. al. 'Myocardial postischemic injury is reduced by polyADPri-pose polymerase-1 gene disruption.' Mol Med 2000 April;6(4):271–82.

Inflammatory response: Lekstrom-Himes J, Xanthopoulos KG 'CCAAT/enhancer binding protein epsilon is critical for effective neutrophil-mediated response to inflammatory challenge.' Blood 1999 May 1;93(9): 3096–105.

Haemophilia B: Crossley M, Brownlee GG 'Disruption of a C/EBP binding site in the factor IX promoter is associated with haemophilia B.' Nature 1990 May 31;345(6274):444–6.

Werner syndrome: Li B, Comai L 'Requirements for the nucleoytic processing of DNA ends by the Werner syndrome protein:Ku70/80 complex.' J Biol Chem Jan. 4, 2001.

Asthma: Nakamura et. al. 'Gene expression of the GATA-3 transcription factor is increased in atopic asthma.' J Allergy Clin Immunol 1999 February;103(2 Pt 1):215–22.

HDR syndrome: Van Esch et. al. 'GATA3 haplo-insufficiency causes human HDR syndrome.' Nature 2000 July 27;406(6794):419–22.

Congenital heart defects: Srivastava D 'HAND proteins: molecular mediators of cardiac development and congenital heart disease.' Trends Cardiovasc Med 1999 January-February;9(1–2):11–8.

Saethre-Chotzen syndrome: El Ghouzzi et. al. 'Mutations within or upstream of the basic helix-loop-helix domain of the TWIST gene are specific to Saethre-Chotzen syndrome.' Eur J Hum Genet 1999 January;7(1):27–33.

Renal disease: Morello et. al. 'Regulation of glomerular basement membrane collagen expression by LMX1B contributes to renal disease in nail patella syndrome.' Nat Genet. 2001 February;27(2):205–208.

Preeclampsia: Rajakumar et. al. 'Selective Overexpression of the Hypoxia-Inducible Transcription Factor, HIF-2alpha, in Placentas from Women with Preeclampsia.' Biol Reprod. 2001 February;64(2):499–506.

Ogata et. al. 'Inducible expression of basic transcription factor-binding protein 2 (BTEB2), a member of zinc finger family of transcription factors, in cardiac allograft vascular disease.' Transplantation. 2000 December 15;70(11):1653–6.

Colorectal cancer: Rask et. al. 'Increased expression of the transcription factors CCAAT-enhancer binding protein-beta (C/EBBeta) and C/EBzeta (CHOP)correlate with invasive-ness of human colorectal cancer.' Int J Cancer. 2000 May 1;86(3):337–43.

Thyroid cancer: Kebebew et. al. 'The helix-loop-helix transcription factor, Id-1, is over-expressed in medullary thyroid cancer' Surgery. 2000 December; 128(6): 952–7.

Esophagal cancer: Saeki et. al. 'Expression of ets-1 transcription factor is correlated with penetrating tumor progression in patients with squamous cell carcinoma of the esophagus' Cancer. 2000 October 15;89(8): 1670–6.

The diversity of mechanisms involved in the regulation of genes provides an alternative level at which to target therapies and diagnosis for diseases. In particular this may be relevant to diseases where current therapies may have unwanted side effects or fail to provide effective treatment. For cancer patients such methods constitute a considerable advantage over conventional methods such as chemotherapy with their massive side effects, which sometimes result in unacceptable morbidity or lead up to the death of the patient. In practice, these unwanted side effects associated with cancer therapies frequently limit the treatment which could help a patient.

A global analysis of the status of gene regulatory mechanisms would provide a basis for the development of appropriate and specific therapies for the many diseases associated with gene regulation. Such analysis may be carried out in a gene specific manner based on the results of gene expression, e.g. DNA micro array analysis of mRNA expression or proteomic analysis. The next step would then be to look at the causal factors involved at earlier stages in the regulatory mechanisms. DNA methylation provides a novel level of information at which to analyse the genome.

5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing since 5-methylcytosine has the same base pairing behavior as cytosine. Moreover, the epigenetic information carried by 5-methylcytosine is completely lost during PCR amplification.

A relatively new and currently the most frequently used method for analyzing DNA for 5-methylcytosine is based upon the specific reaction of bisulfite with cytosine which, upon subsequent alkaline hydrolysis, is converted to uracil which corresponds to thymidine in its base pairing behavior. However, 5-methylcytosine remains unmodified under these conditions. Consequently, the original DNA is converted in such a manner that methylcytosine, which originally could not be distinguished from cytosine by its hybridization behavior, can now be detected as the only remaining cytosine using "normal" molecular biological techniques, for example, by amplification and hybridization or sequencing. All of these techniques are based on base pairing which can now be fully exploited. In terms of sensitivity, the prior art is defined by a method which encloses the DNA to be analyzed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. 1996 Dec. 15;24(24):5064–6). Using this method, it is possible to analyze individual cells, which illustrates the potential of the method. However, currently only individual regions of a length of up to approximately 3000 base pairs are analyzed, a global analysis of cells for thousands of possible methylation events is not possible. However, this method cannot reliably analyze very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26,2255.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. 1997 March-April;5(2): 94–8) the bisulfite technique is only used in research. Always, however, short, specific fragments of a known gene are amplified subsequent to a bisulfite treatment and either completely sequenced (Olek A, Walter J. The pre-implantation ontogeny of the H19 methylation imprint. Nat Genet. 1997 November;17(3):275–6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. 1997 June 15;25(12):2529–31, Patent application WO 95/00669) or by enzymatic digestion (Xiong Z, Laird PW. COBRA: a sensitive and quantitative DNA methylation assay. Nucleic Acids Res. 1997 June 15;25(12):2532–4). In addition, detection by hybridization has also been described (Olek et al., WO 99/28498).

Further publications dealing with the use of the bisulfite technique for methylation detection in individual genes are: Grigg G, Clark S. Sequencing 5-methylcytosine residues in genomic DNA. Bioessays. 1994 June;16(6):431–6, 431; Zeschnigk M, Schmitz B, Dittrich B, Buiting K, Horsthemke B, Doerfler W. Imprinted segments in the human genome: different DNA methylation patterns in the Prader-Willi/ Angelman syndrome region as determined by the genomic sequencing method. Hum Mol Genet. 1997 March;6(3): 387–95; Feil R, Charlton J, Bird AP, Walter J, Reik W. Methylation analysis on individual chromosomes: improved protocol for bisulphite genomic sequencing. Nucleic Acids Res. 1994 February 25;22(4):695–6; Martin V, Ribieras S, Song-Wang X, Rio MC, Dante R. Genomic sequencing indicates a correlation between DNA hypomethylation in the 5' region of the pS2 gene and its expression in human breast cancer cell lines. Gene. 1995 May 19;157(1–2):261-4; WO 97/46705, WO 95/15373 and WO 97/45560.

An overview of the Prior Art in oligomer array manufacturing can be gathered from a special edition of Nature Genetics (Nature Genetics Supplement, Volume 21, January 1999), published in January 1999, and from the literature cited therein.

Fluorescently labeled probes are often used for the scanning of immobilized DNA arrays. The simple attachment of Cy3 and Cy5 dyes to the 5'-OH of the specific probe are particularly suitable for fluorescence labels. The detection of the fluorescence of the hybridized probes may be carried out, for example via a confocal microscope. Cy3 and Cy5 dyes, besides many others, are commercially available.

Matrix Assisted Laser Desorption Ionization Mass Spectrometry (MALDI-TOF) is a very efficient development for the analysis of biomolecules (Karas M, Hillenkamp F. Laser desorption ionization of proteins with molecular masses exceeding 10,000 daltons. Anal Chem. 1988 October 15;60 (20):2299–301). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones.

MALDI-TOF spectrometry is excellently suited to the analysis of peptides and proteins. The analysis of nucleic acids is somewhat more difficult (Gut I G, Beck S. DNA and Matrix Assisted Laser Desorption Ionization Mass Spectrometry. Current Innovations and Future Trends. 1995, 1; 147–57). The sensitivity to nucleic acids is approximately 100 times worse than to peptides and decreases disproportionally with increasing fragment size. For nucleic acids having a multiply negatively charged backbone, the ionization process via the matrix is considerably less efficient. In MALDI-TOF spectrometry, the selection of the matrix plays an eminently important role. For the desorption of peptides, several very efficient matrixes have been found which produce a very fine crystallization. There are now several responsive matrixes for DNA, however, the difference in sensitivity has not been reduced. The difference in sensitivity can be reduced by chemically modifying the DNA in such a manner that it becomes more similar to a peptide. Phosphorothioate nucleic acids in which the usual phosphates of the backbone are substituted with thiophosphates can be converted into a charge-neutral DNA using simple alkylation chemistry (Gut IG, Beck S. A procedure for selective DNA alkylation and detection by mass spectrometry. Nucleic Acids Res. 1995 April 25;23(8):1367–73). The coupling of a charge tag to this modified DNA results in an increase in sensitivity to the same level as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

SUMMARY OF THE INVENTION

The object of the present invention is to provide the chemically modified DNA of genes associated with gene regulation, as well as oligonucleotides and/or PNA-oligomers for detecting cytosine methylations, as well as a method which is particularly suitable for the diagnosis and/or therapy of genetic and epigenetic parameters of genes associated with gene regulation. The present invention is based on the discovery that genetic and epigenetic parameters and, in particular, the cytosine methylation pattern of genes associated with gene regulation are particularly suitable for the diagnosis and/or therapy of diseases associated with gene regulation.

This objective is achieved according to the present invention using a nucleic acid containing a sequence of at least 18 bases in length of the chemically pretreated DNA of genes associated with gene regulation according to one of Seq. ID No.1 through Seq. ID No.224 and sequences complementary thereto and/or a sequence of a chemically pretreated DNA of genes according to table 1 and sequences complementary thereto. In the table, after the listed gene designations, the respective data bank numbers (accession numbers) are specified which define the appertaining gene sequences as unique. GenBank was used as the underlying data bank, which is located at the National Institute of Health, internet address www.ncbi.nlm.nih.gov.

The chemically modified nucleic acid could heretofore not be connected with the ascertainment of genetic and epigenetic parameters.

The object of the present invention is further achieved by an oligonucleotide or oligomer for detecting the cytosine methylation state in chemically pretreated DNA, containing at least one base sequence having a length of at least 13 nucleotides which hybridizes to a chemically pretreated DNA of genes associated with gene regulation according to Seq. ID No.1 through Seq. ID No.224 and sequences complementary thereto and/or a sequence of a chemically pre-treated DNA of genes according to table 1 and sequences complementary thereto. The oligomer probes according to the present invention constitute important and effective tools which, for the first time, make it possible to ascertain the genetic and epigenetic parameters of genes associated with gene regulation. The base sequence of the oligomers preferably contains at least one CpG dinucleotide. The probes may also exist in the form of a PNA (peptide nucleic acid) which has particularly preferred pairing properties. Particularly preferred are oligonucleotides according to the present invention in which the cytosine of the CpG dinucleotide is the $5^{th}$–$9^{th}$ nucleotide from the 5'-end of the 13-mer; in the case of PNA-oligomers, it is preferred for the cytosine of the CpG dinucleotide to be the $4^{th}$–$6^{th}$ nucleotide from the 5'-end of the 9-mer.

The oligomers according to the present invention are normally used in so called "sets" which contain at least one oligomer for each of the CpG dinucleotides of the sequences of Seq. ID No.1 through Seq. ID No.224 and sequences complementary thereto and/or a sequence of a chemically pretreated DNA of genes according to table 1 and sequences complementary thereto. Preferred is a set which contains at least one oligomer for each of the CpG dinucleotides from one of Seq. ID No.1 through Seq. ID No.224 and sequences complementary thereto and/or a sequence of a chemically pretreated DNA of genes according to table 1 and sequences complementary thereto.

Moreover, the present invention makes available a set of at least two oligonucleotides which can be used as so-called "primer oligonucleotides" for amplifying DNA sequences of one of Seq. ID No.1 through Seq. ID No.224 and sequences complementary thereto and/or a sequence of a chemically pretreated DNA of genes according to table 1 and sequences complementary thereto, or segments thereof.

In the case of the sets of oligonucleotides according to the present invention, it is preferred that at least one oligonucleotide is bound to a solid phase.

The present invention moreover relates to a set of at least 10 n (oligonucleotides and/or PNA-oligomers) used for detecting the cytosine methylation state in chemically pretreated genomic DNA (Seq. ID No.1 through Seq. ID No.224 and sequences complementary thereto and/or a sequence of a chemically pretreated DNA of genes according to table 1 and sequences complementary thereto). These probes enable diagnosis and/or therapy of genetic and epigenetic parameters of genes associated with gene regulation. The set of oligomers may also be used for detecting single nucleotide polymorphisms (SNPs) in the chemically pretreated DNA of genes associated with gene regulation according to one of Seq. ID No.1 through Seq. ID No.224 and sequences complementary thereto and/or a sequence of a chemically pretreated DNA of genes to according to table 1 and sequences complementary thereto.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterized in that it is arranged on the solid phase in the form of a rectangular or hexagonal lattice. The solid phase surface is preferably composed of silicon, glass, polystyrene, aluminum, steel, iron, copper, nickel, silver, or gold. However, nitrocellulose as well as plastics such as nylon which can exist in the form of pellets or also as resin matrices are possible as well.

Therefore, a further subject matter of the present invention is a method for manufacturing an array fixed to a carrier material for analysis in connection with diseases associated with gene regulation in which method at least one oligomer according to the present invention is coupled to a solid phase. Methods for manufacturing such arrays are known, for example, from U.S. Pat. No. 5,744,305 by means of solid-phase chemistry and photolabile protecting groups.

A further subject matter of the present invention relates to a DNA chip for the analysis of diseases associated with gene regulation which contains at least one nucleic acid according to the present invention. DNA chips are known, for example, from U.S. Pat. No. 5,837,832.

Moreover, a subject matter of the present invention is a kit which may be composed, for example, of a bisulfite-containing reagent, a set of primer oligonucleotides containing at least two oligonucleotides whose sequences in each case correspond or are complementary to an 18 base long segment of the base sequences specified in the appendix (Seq. ID No.1 through Seq. ID No.224 and sequences complementary thereto and/or a sequence of a chemically pretreated DNA of genes according to table 1 and sequences complementary thereto), oligonucleotides and/or PNA-oligomers as well as instructions for carrying out and evaluating the described method. However, a kit along the lines of the present invention can also contain only part of the aforementioned components.

The present invention also makes available a method for ascertaining genetic and/or epigenetic parameters of genes associated with the cycle cell by analyzing cytosine methylations and single nucleotide polymorphisms, including the following steps:

In the first step of the method, a genomic DNA sample is chemically treated in such a manner that cytosine bases which are unmethylated at the 5'-position are converted to uracil, thymine, or another base which is dissimilar to cytosine in terms of hybridization behavior. This will be understood as 'chemical pretreatment' hereinafter.

The genomic DNA to be analyzed is preferably obtained form usual sources of DNA such as cells or cell components, for example, cell lines, biopsies, blood, sputum, stool, urine, cerebral-spinal fluid, tissue embedded in paraffin such as tissue from eyes, intestine, kidney, brain, heart, prostate, lung, breast or liver, histologic object slides, or combinations thereof.

The above described treatment of genomic DNA is preferably carried out with bisulfite (hydrogen sulfite, disulfite) and subsequent alkaline hydrolysis which results in a conversion of non-methylated cytosine nucleobases to uracil or to another base which is dissimilar to cytosine in terms of base pairing behavior.

Fragments of the chemically pretreated DNA are amplified, using sets of primer oligonucleotides according to the present invention, and a, preferably heat-stable polymerase. Because of statistical and practical considerations, preferably more than ten different fragments having a length of 100–2000 base pairs are amplified. The amplification of several DNA segments can be carried out simultaneously in one and the same reaction vessel. Usually, the amplification is carried out by means of a polymerase chain reaction (PCR).

In a preferred embodiment of the method, the set of primer oligonucleotides includes at least two olignonucleotides whose sequences are each reverse complementary or identical to an at least 18 base-pair long segment of the base sequences specified in the appendix (Seq. ID No.1 through Seq. ID No.224 and sequences complementary thereto and/or a sequence of a chemically pretreated DNA of genes according to table 1 and sequences complementary thereto). The primer oligonucleotides are preferably characterized in that they do not contain any CpG dinucleotides.

According to the present invention, it is preferred that at least one primer oligonucleotide is bonded to a solid phase during amplification. The different oligonucleotide and/or PNA-oligomer sequences can be arranged on a plane solid phase in the form of a rectangular or hexagonal lattice, the solid phase surface preferably being composed of silicon, glass, polystyrene, aluminum, steel, iron, copper, nickel, silver, or gold, it being possible for other materials such as nitrocellulose or plastics to be used as well.

The fragments obtained by means of the amplification can carry a directly or indirectly detectable label. Preferred are labels in the form of fluorescence labels, radionuclides, or detachable molecule fragments having a typical mass which can be detected in a mass spectrometer, it being preferred that the fragments that are produced have a single positive or negative net charge for better detectability in the mass spectrometer. The detection may be carried out and visualized by means of matrix assisted laser desorption/ionization mass spectrometry (MALDI) or using electron spray mass spectrometry (ESI).

The amplificates obtained in the second step of the method are subsequently hybridized to an array or a set of oligonucleotides and/or PNA probes. In this context, the hybridization takes place in the manner described in the following. The set of probes used during the hybridization is preferably composed of at least 10 oligonucleotides or PNA-oligomers. In the process, the amplificates serve as probes which hybridize to oligonucleotides previously bonded to a solid phase. The non-hybridized fragments are subsequently removed. Said oligonucleotides contain at least one base sequence having a length of 13 nucleotides which is reverse complementary or identical to a segment of the base sequences specified in the appendix, the segment containing at least one CpG dinucleotide. The cytosine of the CpG dinucleotide is the $5^{th}$ to $9^{th}$ nucleotide from the 5'-end of the 13-mer. One oligonucleotide exists for each CpG dinucleotide. Said PNA-oligomers contain at least one base sequence having a length of 9 nucleotides which is reverse complementary or identical to a segment of the base sequences specified in the appendix, the segment containing at least one CpG dinucleotide. The cytosine of the CpG dinucleotide is the $4^{th}$ to $6^{th}$ nucleotide seen from the 5'-end of the 9-mer. One oligonucleotide exists for each CpG dinucleotide.

In the fourth step of the method, the non-hybridized amplificates are removed.

In the final step of the method, the hybridized amplificates are detected. In this context, it is preferred that labels attached to the amplificates are identifiable at each position of the solid phase at which an oligonucleotide sequence is located.

According to the present invention, it is preferred that the labels of the amplificates are fluorescence labels, radionuclides, or detachable molecule fragments having a typical mass which can be detected in a mass spectrometer. The mass spectrometer is preferred for the detection of the amplificates, fragments of the amplificates or of probes which are complementary to the amplificates, it being possible for the detection to be carried out and visualized by means of matrix assisted laser desorption/ionization mass spectrometry (MALDI) or using electron spray mass spectrometry (ESI).

The produced fragments may have a single positive or negative net charge for better detectability in the mass spectrometer. The aforementioned method is preferably used for ascertaining genetic and/or epigenetic parameters of genes associated with gene regulation.

The oligomers according to the present invention or arrays thereof as well as a kit according to the present invention are intended to be used for the diagnosis and/or therapy of diseases associated with gene regulationby analyzing methylation patterns of genes associated with gene regulation. According to the present invention, the method is preferably used for the diagnosis and/or therapy of important genetic and/or epigenetic parameters within genes associated with gene regulation.

The method according to the present invention is used, for example, for the diagnosis and/or therapy of severe combined immunodeficiency disease, cardiac disorders, inflammatory response, heamophilia, Werner syndrome, asthma, HDR syndrome, Saethre-Chotzen syndrome, renal disease, preeclampsia, graft-versus-host disease, solid tumors and cancers.

The nucleic acids according to the present invention of Seq. ID No.1 through Seq. ID No.224 and sequences complementary thereto and/or a sequence of a chemically pretreated DNA of genes according to table 1 and sequences complementary thereto can be used for the diagnosis and/or therapy of genetic and/or epigenetic parameters of genes associated with gene regulation.

The present invention moreover relates to a method for manufacturing a diagnostic agent and/or therapeutic agent for the diagnosis and/or therapy of diseases associated with gene regulationby analyzing methylation patterns of genes associated with gene regulation, the diagnostic agent and/or therapeutic agent being characterized in that at least one nucleic acid according to the present invention is used for manufacturing it, possibly together with suitable additives and auxiliary agents.

A further subject matter of the present invention relates to a diagnostic agent and/or therapeutic agent for diseases associated with gene regulationby analyzing methylation patterns of genes associated with gene regulation, the diagnostic agent and/or therapeutic agent containing at least one nucleic acid according to the present invention, possibly together with suitable additives and auxiliary agents.

The present invention moreover relates to the diagnosis and/or prognosis of events which are disadvantageous to patients or individuals in which important genetic and/or epigenetic parameters within genes associated with gene regulation said parameters obtained by means of the present invention may be compared to another set of genetic and/or epigenetic parameters, the differences serving as the basis for a diagnosis and/or prognosis of events which are disadvantageous to patients or individuals.

In the context of the present invention the term "hybridization" is to be understood as a bond of an oligonucleotide to a completely complementary sequence along the lines of the Watson-Crick base pairings in the sample DNA, forming a duplex structure. To be understood by "stringent hybridization conditions" are those conditions in which a hybridization is carried out at 60° C. in 2.5×SSC buffer, followed by several washing steps at 37° C. in a low buffer concentration, and remains stable.

The term "functional variants" denotes all DNA sequences which are complementary to a DNA sequence, and which hybridize to the reference sequence under stringent conditions and have an activity similar to the corresponding polypeptide according to the present invention.

In the context of the present invention, "genetic parameters" are mutations and polymorphisms of genes associated with gene regulationand sequences further required for their regulation. To be designated as mutations are, in particular, insertions, deletions, point mutations, inversions and polymorphisms and, particularly preferred, SNPs (single nucleotide polymorphisms).

In the context of the present invention, "epigenetic parameters" are, in particular, cytosine methylations and further chemical modifications of DNA bases of genes associated with gene regulationand sequences further required for their regulation. Further epigenetic parameters include, for example, the acetylation of histones which, however, cannot be directly analyzed using the described method but which, in turn, correlates with the DNA methylation.

In the following, the present invention will be explained in greater detail on the basis of the sequences and examples with reference to the accompanying figure without being limited thereto.

FIG. 1

FIG. 1 shows the hybridisation of fluorescent labelled amplificates to a surface bound olignonucleotide. Sample I being from pilocytic astrocytoma (brain tumor) tissue and sample II being from grade II astrocytoma (brain tumor) tissue. Flourescence at a spot shows hybridisation of the amplificate to the olignonucleotide. Hybridisation to a CG olignonucleotide denotes methylation at the cytosine position being analysed, hybridisation to a TG olignonucleotide denotes no methylation at the cytosine position being analysed.

Sequence ID Nos. 1 to 224

Sequence ID Nos. 1 to 224 show sequences of genes associated with gene regulation according to the invention. Sequences having odd sequence numbers (e.g., Seq. ID No. 1, 3, 5, . . . ) exhibit in each case sequences of the chemically pretreated genomic DNAs of different genes associated with gene regulation. Sequences having even sequence numbers (e.g., Seq. ID No. 2, 4, 6, . . . ) exhibit in each case the sequences of the chemically pretreated genomic DNAs of genes associated with gene regulationwhich are complementary to the preceeding sequences (e.g., the complementary sequence to Seq. ID No.1 is Seq. ID No.2, the complementary sequence to Seq. ID No.3 is Seq. ID No.4, etc.)

Sequence ID Nos. 225 to 228

Sequence ID Nos. 225 to 228 show the sequences of oligonucleotides used in Example 1.

EXAMPLE 1

Methylation Analysis of the Gene p53 Associated with Gene Regulation.

This example relates to a fragment of a gene associated with gene regulation, in this case, p53 in which a specific CG-position is analyzed for its methylation status.

In the first step, a genomic sequence is treated using bisulfite (hydrogen sulfite, disulfite) in such a manner that all cytosines which are not methylated at the 5-position of the base are modified in such a manner that a different base is substituted with regard to the base pairing behavior while the cytosines methylated at the 5-position remain unchanged.

If bisulfite solution is used for the reaction, then an addition takes place at the non-methylated cytosine bases. Moreover, a denaturating reagent or solvent as well as a radical interceptor must be present. A subsequent alkaline hydrolysis then gives rise to the conversion of non-methylated cytosine nucleobases to uracil. The chemically converted DNA (Seq ID No. 221) is then used for the detection of methylated cytosines. In the second step of the method, the treated DNA sample is diluted with water or an aqueous solution. Preferably, the DNA is subsequently desulfonated (10–30 min, 90–100° C.) at an alkaline pH value. In the third step of the method, the DNA sample is amplified in a polymerase chain reaction, preferably using a heat-resistant DNA polymerase. In the present case, cytosines of the gene p53 are analyzed. To this end, a defined fragment having a length of 595 bp is amplified with the specific primer oligo-nucleotides GTGATAAGGGTTGTGAAGGA (sequence ID No.225) and CAAAAACTTACCCAATCCAA (sequence ID No.226). This amplificate serves as a sample which hybridizes to an oligonucleotide previously bonded to a solid phase, forming a duplex structure, for example AACCCCTACGAAACTCCT (sequence ID No.227), the cytosine to be detected being located at position 401 of the amplificate. The detection of the hybridization product is based on Cy3 and Cy5 flourescently labeled primer oligonucleotides which have been used for the amplification. A hybridization reaction of the amplified DNA with the oligonucleotide takes place only if a methylated cytosine was present at this location in the bisulfite-treated DNA. Thus, the methylation status of the specific cytosine to be analyzed is inferred from the hybridization product.

In order to verify the methylation status of the position, a sample of the amplificate is further hybridized to another oligonucleotide previously bonded to a solid phase. Said olignonucleotide is identical to the oligonucleotide previously used to analyze the methylation status of the sample, with the exception of the position in question. At the position to be analysed said oligonucleotide comprises a thymine base as opposed to a cytosine base i.e. sequence AACCCCTACAAAACTCCT (sequence ID No.228). Therefore, the hybridization reaction only takes place if an unmethylated cytosine was present at the position to be analysed.

The analysis was carried out on two tissue samples, Sample I from pilocytic astrocytoma (brain tumor) tissue, and Sample 2 from grade II astrocytoma (brain tumor) tissue. From the results (FIG. 1) it can be seen that Sample 2 was methylated at position 401 of the amplificate whereas Sample 1 contained a mixture of both methylated and unmethylated cells at the same position.

EXAMPLE 2

Diagnosis of Diseases Associated with Gene Regulation

In order to relate the methylation patterns to one of the diseases associated with gene regulation, it is initially required to analyze the DNA methylation patterns of a group of diseased and of a group of healthy patients. These analyses are carried out, for example, analogously to example 1. The results obtained in this manner are stored in a database and the CpG dinucleotides which are methylated differently between the two groups are identified. This can be carried out by determining individual CpG methylation rates as can be done, for example, in a relatively imprecise manner, by sequencing or else, in a very precise manner, by a methylation-sensitive "primer extension reaction". It is also possible for the entire methylation status to be analyzed simultaneously, and for the patterns to be compared, for example, by clustering analyses which can be carried out, for example, by a computer.

Subsequently, it is possible to allocate the examined patients to a specific therapy group and to treat these patients selectively with an individualized therapy.

Example 2 can be carried out, for example, for the following diseases: severe combined immunodeficiency disease, cardiac disorders, inflammatory response, heamophilia, Werner syndrome, asthma, HDR syndrome, Saethre-Chotzen syndrome, renal disease, preeclampsia, graft-versus-host disease, solid tumors and cancers.

TABLE 1

Listing of preferred genes associated with gene regulation according to the invention.

| Gene | Database entry No. (GenBank) |
| --- | --- |
| CBFB | (L20298), |
| ELF1 | (M82882), |
| ETV3 | (L16464), |
| ETV4 | (D12765), |
| LYL1 | (M22637), |
| RENBP | (U52112), |
| TAF2C2 | (Y09321), |
| TCF3 | (M31222), |
| H4FI | (NM_003544), |
| ADA | (NM_000022), |
| ATF3 | (NM_001674), |
| CEBPD | (NM_005195), |
| CHD1L | (NM_004284), |
| CTPS | (NM_001905), |
| DCTD | (NM_001921), |
| EIF2B1 | (NM_001414), |
| ELF3 | (NM_004433), |
| ELK4 | (NM_021795), |
| ETV5 | (NM_004454), |
| FOXO1A | (NM_002015), |
| HIVEP1 | (NM_002114), |
| HMG2 | (NM_002129), |
| ID1 | (NM_002165), |
| ID3 | (NM_002167), |
| ID4 | (NM_001546), |
| LAF4 | (NM_0022859), |
| MAFG | (NM_002359), |
| MHC2TA | (NM_000246), |
| ODC1 | (NM_002539), |
| PBX3 | (NM_006195), |
| PCNA | (NM_002592), |
| POU2AF1 | (NM_006235), |
| PRPS1 | (NM_002764), |
| RARG | (NM_000966), |
| RECQL | (NM_002907), |
| RXRA | (NM_002957), |
| TIAL1 | (NM_003252), |
| ZNF173 | (NM_003449), |
| ATBF1 | (NM_006885), |
| FLI1 | (NM_002017), |
| NUMA1 | (NM_006185), |
| POU2F2 | (NM_002698), |
| SF100 | (NM_003113) |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07195870B2). An electronic copy of the "Sequence Listing" will also be available from the USPTO upon request and payment of the fee set forth in 37 CFR 1.19(b)(3).

What is claimed is:

1. A method for diagnosis and/or prognosis of, or predisposition to a condition or disease comprising:
    converting, in a genomic DNA sample and by chemical treatment, cytosine bases that are unmethylated at the 5-position to uracil or another base dissimilar to cytosine in terms of hybridization behavior to provide chemically pretreated genomic DNA;
    amplifying fragments of the chemically pretreated genomic DNA having a sequence selected from the group consisting of SEQ ID NOS:49, 50 and complements, and portions thereof, using at least one set of primer oligonucleotides and a polymerase to produce amplificates;
    hybridising the amplificates to at least one set of detection oligomers;
    detecting the hybridised amplificates; and
    determining, based on the detection, the methylation status of at least one CpG dinucleotide of the CBFB genomic sequence corresponding to treated SEQ ID NOS:49, 50 and complements thereof, wherein a diagnosis and/or prognosis of, or predisposition to a condition or disease associated with CBFB is afforded, and wherein the condition or disease is a CBFB-associated cancer.

2. The method of claim 1, wherein amplifying the fragments of chemically pretreated genomic DNA using a set of primer oligonucleotides and a polymerase is performed such that the amplificates carry a detectable label.

3. The method of claim 1, wherein hybridising the amplificates to the at least one set of detection oligomers comprises hybridizing wherein the base sequence of the oligomers includes at least one CpG dinucleotide.

4. The method of claim 3, wherein the detection oligomers are oligonucleotides.

5. The method of claim 3, wherein the detection oligomers are PNA probes.

6. The method of claim 3, wherein the detection oligomers are in an array.

7. The method of claim 3, wherein the cytosine of the CpG dinucleotide is located approximately in a middle third of each detection oligomer.

8. The method of claim 3, wherein the set of oligomers comprises at least two different detection oligomers.

9. The method of claim 3, wherein the at least one set of detection oligomers comprises oligomers for detecting the methylation state of at least one CpG dinucleotide of a sequence selected from the group consisting of SEQ ID NOS:49, 50 and complements, and portions thereof.

10. The method of claim 1, wherein the chemical treatment is carried out using a bisulfite reagent.

11. The method of claim 1, wherein the amplified fragments comprise more than ten different fragments having a length of from 100 to 2,000 base pairs.

12. The method of claim 1, wherein amplifying the fragments of the chemically pretreated genomic DNA comprises amplifying more than one DNA segment in one reaction vessel.

13. The method of claim 1, wherein the at least one set of primer oligonucleotides comprises oligonucleotides having at least one contiguous base sequence of at least 9 nucleotides in length that hybridizes to or is identical with a chemically pretreated genomic DNA sequence selected from the group consisting of SEQ ID NOS:49, 50 and complements, and portions thereof.

14. The method of claim 1, wherein the polymerase is a heat-resistant DNA polymerase.

15. The method of claim 1, wherein amplifying the fragments of the chemically pretreated genomic DNA comprises use of a polymerase chain reaction (PCR).

16. The method of claim 2, wherein the detectable label is selected from the group consisting of fluorescent labels, radionuclides and detachable molecule fragments having a predetermined mass detectable in a mass spectrometer.

17. The method of claim 1, further comprising detecting amplificates or fragments of the amplificates in a mass spectrometer.

18. The method of claim 17, wherein the produced fragments comprise a single positive or negative net charge.

19. The method of claim 17, wherein the mass spectrometer uses matrix assisted laser desorption/ionization mass spectrometry (MALDI) or an electron spray mass spectrometry (ESI).

20. The method of claim 1, wherein the genomic DNA is obtained from cells or cellular components which contain DNA.

21. The method of claim 1, wherein the genomic DNA is obtained from a source selected from the group consisting of cell lines, biopsies, blood, sputum, stool, urine, cerebral-spinal fluid, tissue embedded in paraffin, intestine, kidney, brain, heart, prostate, lung, breast, liver, histologic object slides and combinations thereof.

22. The method of claim 1, further comprising treating the condition or disease associated with CBFB, based on the diagnosis and/or prognosis of, or predisposition to the condition or disease associated with CBFB.

* * * * *